(12) United States Patent
Reichwagen

(10) Patent No.: US 10,973,919 B2
(45) Date of Patent: *Apr. 13, 2021

(54) VITAMIN PREPARATION

(71) Applicant: Hilatrade AG, Hunenberg (CH)

(72) Inventor: Sven Reichwagen, Ahlen (DE)

(73) Assignee: Hilaltrade AG, Hünenberg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/417,288

(22) PCT Filed: Jul. 23, 2013

(86) PCT No.: PCT/EP2013/065477
§ 371 (c)(1),
(2) Date: Aug. 17, 2015

(87) PCT Pub. No.: WO2014/016277
PCT Pub. Date: Jan. 30, 2014

(65) Prior Publication Data
US 2015/0366971 A1 Dec. 24, 2015

(30) Foreign Application Priority Data
Jul. 24, 2012 (DE) .......................... 102012014581.0

(51) Int. Cl.
| A61K 47/26 | (2006.01) |
| A61K 8/86 | (2006.01) |
| A61K 8/41 | (2006.01) |
| A61K 8/67 | (2006.01) |
| A61K 31/714 | (2006.01) |
| A61Q 19/00 | (2006.01) |
| A61K 31/7056 | (2006.01) |

(52) U.S. Cl.
CPC ............. *A61K 47/26* (2013.01); *A61K 8/41* (2013.01); *A61K 8/673* (2013.01); *A61K 8/86* (2013.01); *A61K 31/7056* (2013.01); *A61K 31/714* (2013.01); *A61Q 19/00* (2013.01); *A61K 2800/75* (2013.01)

(58) Field of Classification Search
None
See application file for complete search history.

(56) References Cited

U.S. PATENT DOCUMENTS

| 2003/0144198 A1* | 7/2003 | Collins | A61K 31/714 |
| | | | 514/52 |
| 2005/0238675 A1* | 10/2005 | Li | A23L 1/303 |
| | | | 424/400 |
| 2005/0261367 A1* | 11/2005 | Murad | A61K 31/198 |
| | | | 514/492 |
| 2006/0018847 A1* | 1/2006 | Kroepke | A01N 47/44 |
| | | | 424/59 |
| 2008/0039422 A1* | 2/2008 | Cruz | A61K 9/0019 |
| | | | 514/52 |
| 2008/0233180 A1* | 9/2008 | Zeltman | A61K 9/7061 |
| | | | 424/449 |
| 2011/0135714 A1* | 6/2011 | Shin | A61K 9/0014 |
| | | | 424/450 |

FOREIGN PATENT DOCUMENTS

| CN | 101181289 A | * | 5/2008 | ............ A61K 31/07 |
| CN | 102048678 A | * | 5/2011 | ........... A61K 31/216 |
| CN | 102068453 A | * | 5/2011 | ........... A61K 31/164 |
| JP | 2011153083 A | * | 8/2011 | ........... A61K 31/198 |

OTHER PUBLICATIONS

Som I, Bhatia K, M. Status of surfactants as penetration enhancers in transdermal drug delivery. J Pharm Bioall Sci 2012;4:2-9.*
Ebner, F., Heller, A., Rippke, F., & Tausch, I. (2002). Topical use of dexpanthenol in skin disorders. American journal of clinical dermatology, 3(6), 427-433. (Year: 2002).*
Prasad, A. S. (2008). Clinical, immunological, anti-inflammatory and antioxidant roles of zinc. Experimental gerontology, 43(5), 370-377. (Year: 2008).*
Strudwick et al., Diagram of human skin showing differentiated keratinocytes of the epidermis, 2015, retrieved from https://plos.figshare.com/articles/_Diagram_of_human_skin_showing_differentiated_keratinocytes_of_the_epidermis_and_expression . . . /1378021. (Year: 2015).*

* cited by examiner

*Primary Examiner* — Dale R Miller
(74) *Attorney, Agent, or Firm* — Brooks Kushman P.C.

(57) ABSTRACT

The invention relates to a vitamin preparation, especially for application to the skin, containing
- a physiologically effective amount of vitamin B12 or another precursor of coenzyme B12,
- a polysorbate as well as
- customary carrier substances for the formation of a gel matrix.

14 Claims, No Drawings

VITAMIN PREPARATION

The invention relates to a vitamin preparation, particularly in gel form for application to the skin, said preparation containing a physiologically effective amount of vitamin B12 or a precursor thereof.

Vitamin B12 belongs to the group of cobalamins and is an essential vitamin the human or animal body is unable to synthesis. The human need in this respect must therefore be satisfied through food. Cobalamins in sufficient amount are especially found in animal-derived foods. However, their origin is always of bacterial nature.

As a rule, vitamin B12 is understood to mean cyanocobalamin. Additional forms are, for example, aquocobalamin, hydroxycobalamin, and methylcobalamin that is usually found in somatic cells. Functioning and being effective as coenzyme B12 is 5'-deoxyadenosylcobalamin. The active forms methylcobalamin and adenosylcobalamin are formed in the body from the other forms.

Within the meaning of the invention especially cyanocobalamin which is customarily referred to as vitamin B12 shall be understood to be vitamin B12 but also the other precursor forms of the coenzyme B12 as they are indicated above.

For the treatment of a number of skin diseases vitamin B12 has proven to be very effective. It is applied in ointment form for a number of dermatoses, and also for treating atopic eczema. A synthetic or vegetable oil or fat, in particular avocado oil, serves as ointment basis.

Although with customary ointments on oil or fat basis the respective active agent can be satisfactorily spread on the skin portions to be treated their distribution, however, is only superficial. An appreciable transdermal effect cannot be produced.

It is, therefore, the objective of the present invention to propose a vitamin preparation which is capable of introducing vitamin B12 also into the upper skin layers, i.e., the epidermis, where a sustainable effect can then be brought about.

This objective is achieved with a vitamin preparation of the kind first mentioned above that contains a physiologically effective amount of vitamin B12 or another cobalamin, a polysorbate as well as the usual carrier substances needed to establish a carrier matrix.

Polysorbates are surfactants that comprise polar and non-polar constituents. As a result of their composition they are suited to serve as entrainers and it is this characteristic that is made use of here. As polysorbate the customary and commercially available products may be employed. These are multiply ethoxylated sorbitan fatty acid esters of various fatty acids, for example of lauric acid, palmitic acid, stearic acid, oleic acid, and isostearic acid. Monoesters or triesters may be used for this purpose. The number of the polyoxyethylene units is variable but, as a rule, is 4, 5 or 20.

The polysorbate preferred according to the invention is polysorbate 20, a polyoxyethylene sorbitan monolaurate with 20 oxyethylene units which is known under the tradename of Tween®.

In addition to vitamin B12 or another precursor of the coenzyme B12 the vitamin preparation proposed by the present invention contains customary carrier substances to enable a carrier matrix, in particular a gel matrix, to be formed. Such substances are, for example, glycerin, hydroxyethyl cellulose, urea, and demineralized water. For the pH adjustment, preferably to pH 5.4, citric acid and/or caustic soda solution may be employed which have proven to be highly biocompatible. However, other acids and bases may be used as well. The preparation may also be provided in the form of a lotion, cream, ointment, spray, tincture or as shampoo.

The inventive vitamin preparation contains vitamin B12 or another form of cobalamin in an amount ranging between 40 and 100 mg, in particular in an amount of 70 mg per 100 g of the preparation. The polysorbate is contained in an amount ranging between 20 and 100 mg per 100 g of the preparation, in particular in an amount of 40 mg.

For gel formation especially hydroxyethyl cellulose 400 is used in an amount ranging between 1000 mg and 5000 mg per 100 g of the preparation. Further constituents may be glycerin in an amount of between 1000 mg and 5000 mg per 100 g as well as urea in an amount ranging between 2000 mg and 7000 mg per 100 g.

Aside from the above mentioned ingredients the preparation may also contain an antiseptic agent, for example polyhexanide. This shall be added in the form of a commercially available solution concentrate (20% m/v) and is preferably contained in an amount ranging between 100 and 500 mg of concentrate per 100 g. The addition of polyhexanide may be especially helpful in the event of inflamed and inflammable skin diseases during which attacks of microorganisms are encountered. Polyhexanide is an antiseptic on the basis of polyhexamethylene biguanide (PHMB).

The vitamin preparation may contain further active agents beneficial in the treatment of the skin. An example in this context is dexpanthenol which is also a vitamin precursor. In the body, this agent is converted into pantothenic acid which is a vitamin stemming from the group of the B-vitamins (vitamin B5).

Dexpanthenol for example is contained in the preparation in an amount of between 1000 mg and 10000 mg pro 100 g. If thought expedient additional constituents may be polyethylene glycol 400 as well as sodium ascorbate as oxidation inhibitor. The formulation may contain further substances which have proven their worth in the treatment of skin diseases. Examples in this context are taurine, caffeine, lysine, creatine, but also zinc salts, for example zinc sulfate.

Especially zinc sulfate is a long-known agent used for the treatment of eczema and may, for instance, be contained in the preparation in an amount of between 50 and 1000 mg/100 g.

The vitamin preparation proposed by the invention has preferably the following composition:
50 to 500 mg polyhexanide in 20% aqueous solution
20 to 100 mg of polysorbate
1000 to 5000 mg of glycerin
500 to 5000 mg of hydroxyethyl cellulose 400
2500 to 7000 mg of urea
citric acid for buffering to pH 5.4
NaOH for buffering to pH 5.4 as well as
demineralized wafer ad 100 g.

The inventive vitamin preparation may be applied to the skin as a gel but may also be contained in gel form in a plaster/band-aid or pad which is then applied to the skin. Said preparation may also be administered or applied via sprays or as a tincture, for example in the form of nasal spray or eyedrops. Besides being effective in treating dermatoses and eczema it was found that the preparation had a favorable effect on other types of skin and mucous membrane irritations, in particular for allergy-related irritations such as pollen allergies, house-dust allergy, and allergic reactions as a result of insect stings.

Another application field is the cleaning, care, and hypoallergenic impregnation of contact lenses.

The invention is explained in more detail by way of the following examples:

EXAMPLE 1

A vitamin preparation in gel form was produced using the following constituents:

| | | |
|---|---|---|
| 1. Vitamin B12 (cyanocobalamin) | | 70 mg |
| 2. Polyhexanide solution concentrate 20% (m/V) | | 200 mg |
| 3. Polysorbate 20 | | 40 mg |
| 4. Glycerin | | 2500 mg |
| 5. Hydroxyethyl cellulose depending on the desired consistency | | 400 up to 5000 mg. |
| 6. Urea | | 5000 mg |
| 7. Citric acid for buffering to pH 5.4 | | 300 mg |
| 8. If expedient, NaOH for buffering to pH 5.4 | | |
| 9. Demineralized water ad 100 g | | |

The constituents are moderately heated and mixed and then stirred to produce a gel.

EXAMPLE 2

The preparation listed in Example 1 is supplemented by 5000 mg of dexpanthenol and 2000 mg of PEG400.

Further constituents may be admixed, for example 300 mg of taurine, 25 mg of caffeine, 1000 mg of lysine, 500 g of zinc sulfate, and/or 500 mg of creatine. Sodium ascorbate is added in case an oxidation inhibitor is needed.

EXAMPLE 3

Antiallergenic eyedrops were prepared as follows:

| | |
|---|---|
| 1. Vitamin B12 | 70 mg |
| 2. Dexpanthenol | 500 mg |
| 3. Polyhexanide (solution concentrate 20% (m/V)) | 0.75 mg |
| 4. Polysorbate 20 | 40 mg |
| 5. HPMC | 10 mg |
| 6. Trisodium citrate | 10 mg |
| 7. Citric acid ad pH 7.2 | |
| 8. Sodium hydroxide ad pH 7.2 | |
| 9. Sodium chloride for adjustment to 300 mosmol | |
| 10. Demineralized water ad 100 g | |

EXAMPLE 4

An agent for contact lens care was prepared as follows:

| | |
|---|---|
| 1. Vitamin B12 | 70 mg |
| 2. Polyhexanide (solution concentrate 20% (m/V)) | 0.75 mg |
| 3. Polysorbate 20 | 40 mg |
| 4. HPMC | 10 mg |
| 5. Trisodium citrate | 10 mg |
| 6. Citric acid ad pH 7.2 | |
| 7. Sodium hydroxide ad pH 7.2 | |
| 8. Sodium chloride for adjustment to 300 mosmol | |
| 9. Demineralized water ad 100 g | |

EXAMPLE 5

Nasal spray/drops were prepared according to the following formulation:

| | |
|---|---|
| 1. Vitamin B12 (cyanocobalamin) | 70 mg |
| 2. Dexpanthenol | 500 mg |
| 3. Polyhexanide (solution concentrate 20% (m/V)) | 0.15 mg |
| 4. Polysorbate 20 | 40 mg |
| 5. HPMC | 100 mg |
| 6. Trisodium citrate | 25 mg |
| 7. Citric acid ad pH 7.2 | |
| 8. Sodium chloride to achieve a hypertonic decongestant solution | 0.9 to 2.0 g |
| 9. Demineralized water ad 100 g | |

Patient Study

Seven patients suffering from neurodermatitis with eczema on palms, arms, and partially face causing considerable itchiness were treated topically with the gel described in Example 1. Immediately after treatment the itchiness abated and disappeared after a few minutes. Pustules and swellings disappeared after one day, redness on the following day at the latest.

Administering the gel to five patients suffering from psoriasis resulted in the immediate abatement of the itchiness and diminishing of the redness the clay after. Treatment of two patients with dermatoses on the head resulted in dermatoses disappearing within a week.

A preparation according to Example 3 was administered to the eyes of ten allergic persons suffering from conjunctivitis due to airborne pollen. The itchiness disappeared immediately, the signs of inflammation most widely disappeared after three hours at the latest.

The invention claimed is:

1. A method of treating skin, comprising applying to the skin a vitamin preparation containing:
   vitamin B12 or a precursor thereof in an amount in the range of 40 to 100 mg per 100 g of the preparation,
   polysorbate 20 in an amount limited to the range of 20 to 100 mg per 100 g of the preparation as an entrainer, and
   customary carrier substances for the formation of a carrier matrix designed for the application of the preparation to the skin, and
   limiting the range of the vitamin B12 or precursor to an amount whereby to introduce said vitamin B12 or the precursor thereof into layers of skin consisting essentially of the epidermis.

2. A method according to claim 1 wherein said preparation contains polyhexanide.

3. A method according to claim 2 wherein said preparation contains 50 to 500 mg of a 20% polyhexanide solution per 100 g of the preparation.

4. A method according to claim 1 wherein said preparation contains urea.

5. Vitamin preparation according to claim 1 wherein said preparation contains a zinc salt.

6. A method according to claim 1 wherein said preparation contains 50 to 1000 mg of zinc salt per 100 g of the preparation.

7. A method according to claim 1 wherein said preparation contains taurine, lysine, caffeine, and/or creatine.

8. A method according to claim 1 wherein said preparation contains dexpanthenol.

9. A method according to claim 8 wherein said preparation contains 500 to 10000 mg of dexpanthenol per 100 g of the preparation.

10. A method according to claim 1 in which the vitamin preparation is in gel form and wherein said preparation contains
- 40 to 100 mg of vitamin B12 or another precursor of coenzyme B12
- 50 to 500 mg polyhexanide in 20% aqueous solution
- 20 to 100 mg of polysorbate 20
- 1000 to 5000 mg of glycerin
- 500 to 5000 mg of hydroxyethyl cellulose 400
- 2500 to 7000 mg of urea
- citric acid for buffering to pH 5.4
- NaOH for buffering to pH 5.4 as well as
- demineralized water ad 100 g.

11. A method according to claim 10 wherein said preparation additionally contains 1000 mg to 4000 mg of PEG400.

12. A method according to claim 1 wherein said preparation is contained on/in a pad for application to the skin, as spray or tincture for application to mucous membranes.

13. A method according to claim 12 for the treatment of irritation phenomena of the skin and mucous membranes.

14. A method for treating skin, comprising applying to the skin a vitamin preparation containing:
- vitamin B12 or a precursor thereof in an amount in the range of 40 to 100 mg per 100 g of the preparation,
- polysorbate 20 in an amount limited to the range of 20 to 100 mg per 100 g of the preparation as an entrainer,
- dexpanthenol, and
- customary carrier substances for the formation of a carrier matrix designed for the application of the preparation to the skin, and
- limiting the range of the vitamin B12 or precursor to an amount whereby to introduce said vitamin B12 or the precursor thereof into layers of skin consisting essentially of the epidermis.

* * * * *

UNITED STATES PATENT AND TRADEMARK OFFICE
CERTIFICATE OF CORRECTION

PATENT NO. : 10,973,919 B2
APPLICATION NO. : 14/417288
DATED : April 13, 2021
INVENTOR(S) : Sven Reichwagen Page 1 of 1

It is certified that error appears in the above-identified patent and that said Letters Patent is hereby corrected as shown below:

On the Title Page

(73) Assignee should be corrected to read:
Mavena International AG, Hünenberg (CH); and Hilaltrade AG, Hünenberg (CH)

Signed and Sealed this
Seventh Day of February, 2023

Katherine Kelly Vidal
*Director of the United States Patent and Trademark Office*